(12) United States Patent
Alam et al.

(10) Patent No.: US 10,131,707 B2
(45) Date of Patent: Nov. 20, 2018

(54) TREATMENT OF SEPSIS AND SEPTIC SHOCK

(71) Applicant: THE GENERAL HOSPITAL CORPORATION, Boston, MA (US)

(72) Inventors: Hasan B. Alam, Ann Arbor, MI (US); Yongqing Li, Ann Arbor, MI (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 15/106,550

(22) PCT Filed: Jan. 30, 2015

(86) PCT No.: PCT/US2015/013683
§ 371 (c)(1),
(2) Date: Jun. 20, 2016

(87) PCT Pub. No.: WO2015/116896
PCT Pub. Date: Aug. 6, 2015

(65) Prior Publication Data
US 2016/0333081 A1    Nov. 17, 2016

Related U.S. Application Data

(60) Provisional application No. 61/934,051, filed on Jan. 31, 2014.

(51) Int. Cl.
| | | |
|---|---|---|
| *A61K 39/00* | (2006.01) | |
| *A61K 39/395* | (2006.01) | |
| *A61K 31/155* | (2006.01) | |
| *C07K 16/18* | (2006.01) | |
| *C07K 16/44* | (2006.01) | |

(52) U.S. Cl.
CPC ............ *C07K 16/18* (2013.01); *A61K 31/155* (2013.01); *A61K 39/3955* (2013.01); *C07K 16/44* (2013.01); *C07K 2317/76* (2013.01)

(58) Field of Classification Search
CPC .......... A61K 39/3955; A61K 2039/505; A61K 31/155; C07K 16/18; C07K 16/44; C07K 2317/76
See application file for complete search history.

(56) References Cited

FOREIGN PATENT DOCUMENTS

WO    2011/070172 A1    6/2011
WO    2012/0166611 A2    12/2012

OTHER PUBLICATIONS

Li et al., "Surviving lethal septic shock without fluid resuscitation in a rodent model", Surgery 148(2):246-254 (2010).
Brinkmann et al.,"Neutrophil Extracellular Traps Kill Bacteria", Science 303:1532-1535 (2004).
Guimaraes-Costa et al., "ETosis: A Microbicidal Mechanism beyond Cell Death", Journal of Parasitology Research 2012:92743(1-11) (2012).
Li et al., "Identification of Cit H3 as a Potential Serum Protein Biomarker in a Lethal Model of LPS-induced Shock", Surgery 150(3):442-451 (2011).
Li et al., "Protective Effect of Suberolyanilide Hydroxamic Acid Against LPS-Induced Septic Shock in Rodents", Shock 32(5):517-523 (2009).
Neeli et al., "Histone Deimination as a Response to Inflammatory Stimuli in Neutrophils", The Journal of Immunology 180:1895-1902 (2009).
Slack et al., "Protein Arginine Deiminase 4: a target for an epigenetic cancer therapy", Cellular Mol Life Sci. 68(4):709-720 (2011).
Wang et al., "Histone hypercitrullination mediates chromatin decondensation and neutrophil extracellular trap formation", J. Cell Biol. 184(2):205-213 (2009).
Xu et al., "Extracellular histones are major mediators of death in sepsis", Nature Medicine 15(11):1318-1321 (2009).

*Primary Examiner* — Robert S Landsman
*Assistant Examiner* — Bruce D. Hissong
(74) *Attorney, Agent, or Firm* — Nixon Peabody LLP; David S. Resnick; Nicole D. Kling

(57) ABSTRACT

The technology described herein is directed to the treatment of sepsis and/or septic shock by, e.g. administering an agent that can reduce the level of circulating citrullated histones.

6 Claims, 2 Drawing Sheets
Specification includes a Sequence Listing.

SEQUENCE LISTING

```
<160> NUMBER OF SEQ ID NOS: 3

<210> SEQ ID NO 1
<211> LENGTH: 30
<212> TYPE: PRT
<213> ORGANISM: Unknown
<220> FEATURE:
<223> OTHER INFORMATION: Description of Unknown:
      Histone 113 sequence

<400> SEQUENCE: 1

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro
            20                  25                  30

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Gly Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 3

His His His His His His
1               5
```

TREATMENT OF SEPSIS AND SEPTIC SHOCK

CROSS-REFERENCE TO RELATED APPLICATIONS

This application is a 35 U.S.C. § 371 National Phase Entry Application of International Application No. PCT/US2015/013683 filed Jan. 30, 2015, which designates the U.S. and claims benefit under 35 U.S.C. § 119(e) of U.S. Provisional Application No. 61/934,051 filed Jan. 31, 2014, the contents of which are incorporated herein by reference in their entirety.

GOVERNMENT SUPPORT

This invention was made with Government support under grant number GM084127 awarded by the National Institutes of Health. The Government has certain rights in this invention.

SEQUENCE LISTING

The instant application contains a Sequence Listing which has been submitted electronically in ASCII format and is hereby incorporated by reference in its entirety. Said ASCII copy, created on Mar. 12, 2018, is named 030258-080742-US_SL.txt and is 1,108 bytes in size.

TECHNICAL FIELD

The technology described herein relates to the treatment of sepsis and/or septic shock.

BACKGROUND

Sepsis is a lethal condition that is often associated with a serious microbial infection. However, while many hypotheses have been put forward, the exact cause of septic shock is not agreed upon and therapeutics based on targeting the source of these various hypotheses have generally failed in (or prior to) clinical trials. The current treatment generally includes administration of antibiotics.

SUMMARY

The inventors have discovered that the citrullation of histones contributes to the pathology of sepsis. The inventors have further discovered that reducing the level of citrullated histones, by a variety of approaches, reduces the severity and mortality of sepsis and septic shock. Accordingly, provided herein are methods of treating sepsis and/or septic shock by administering inhibitors of citrullated histones.

In one aspect, described herein is a method of treating sepsis and/or septic shock in a subject in need thereof, the method comprising administering a therapeutically effective amount of an inhibitor of citrullated histones to the subject. In some embodiments, the inhibitor of citrullated histones is an inhibitor of protein citrullation. In some embodiments, the inhibitor of citrullated histones is an inhibitor of a peptidyl arginine dehninase (PAD). In some embodiments, the PAD is selected from the group consisting of PAD2 and PAD4. In some embodiments, the inhibitor of protein citrullation is selected from the group consisting of: amidine-based inhibitors; Cl-amidine; F-amidine; biphenyl tetrazole tert-butyl Cl-amidine; YW3-56; o-F-amidine; 1,2,3-triazole peptidomimetic-based inhibitors; 2-chloroacetamidine (2CA); N-a-benzoyl-N5-(2 Chloro-1-iminoethyl)-L-Ornithine amide; ruthenium red; benzoyl-L-arginine amide (BAA); BA; BAEE; BAME; streptonigrin; and ML325.

In some embodiments, the inhibitor of citrullated histones is an antibody reagent that specifically binds citrullated histones. In some embodiments, the antibody reagent specifically binds a citrullated histone and does not specifically bind the corresponding uncitrullated histone.

In some embodiments, the citrullated histone is citrullated H3 or citrullated H4. In some embodiments, the level of a citrullated histone is the level of circulating citrullated histone. In some embodiments, the administration is intravenous. In some embodiments, the subject is a subject identified to have an elevated level of citrullated histone.

BRIEF DESCRIPTION OF THE DRAWINGS

FIG. 4 depicts a schematic demonstrating that histone acetylation can disrupt the PAD substrate recognition motif and thereby prevent the citrullination of adjacent arginine residues.

DETAILED DESCRIPTION

Figure 1:
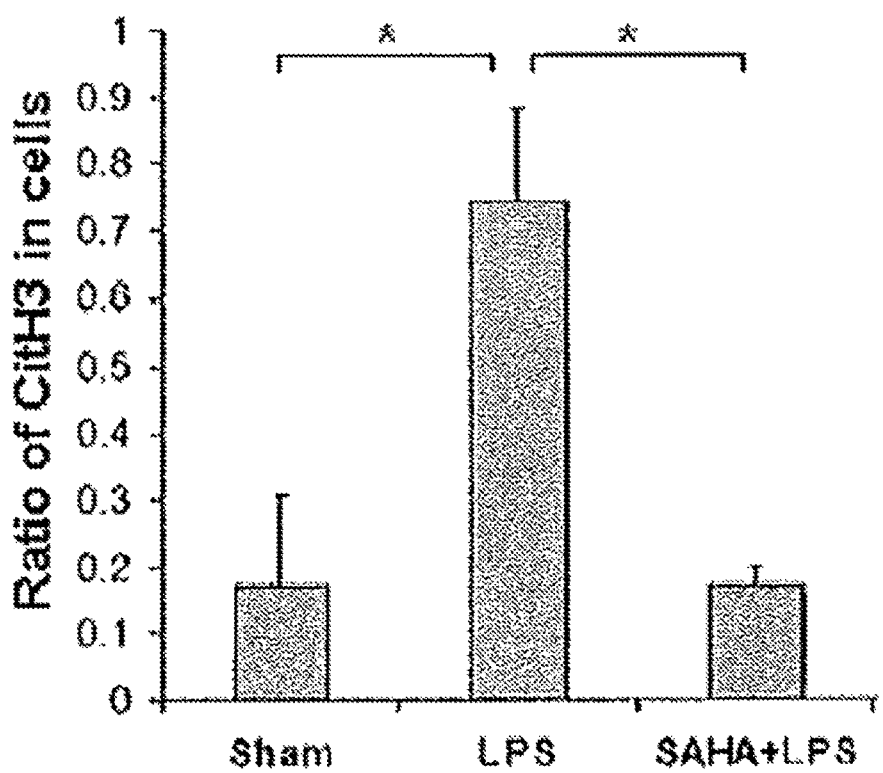
FIG. 1 demonstrates that SAHA suppresses LPS-induced Cit H3 production. Depicted is a graph of the ratio of Cit H3 positive cells to all cells. Statistical analysis shows that the suppression of LPS-induced Cit H3 production by SAHA is significant (n=3; P<0.05).

As described herein, the inventors have discovered that increased levels of citrullated histones in subjects with sepsis contribute to the inflammatory processes and that reducing the levels of citrullated histones reduces the severity and mortality of sepsis.

In one aspect, described herein is a method of treating sepsis and/or septic shock in a subject in need thereof, the method comprising administering a therapeutically effective amount of an inhibitor of citrullated histones to the subject. As used herein, "sepsis" refers to a body or subject's response to a systemic microbial infection, e.g., a widespread inflammatory response caused by infection. The onset of sepsis occurs when rapidly growing infectious agents saturate the blood and overcome a subject's immunological clearance mechanisms. Most existing therapies are ineffective, and subjects can die because of clot formation, hypoperfusion, shock, and multiple organ failure. As used herein, "septic shock" refers to sepsis which has advanced to the point of resulting in a significant drop in blood pressure. In some embodiments, the low blood pressure is not responsive to intravenous fluid administration.

In some embodiments, the methods described herein relate to treating a subject having or diagnosed as having sepsis or septic shock. Subjects having sepsis can be identified by a physician using current methods of diagnosing sepsis. Symptoms and/or complications of sepsis which characterize these conditions and aid in diagnosis are well known in the art and include but are not limited to, fever, elevated heart rate, elevated breathing rate, confusion, pneumonia, painful urination, or low blood pressure. Tests that may aid in a diagnosis of, e.g. sepsis include, but are not limited to, white blood cell counts and blood cultures. Exposure to risk factors for sepsis (e.g. burns or trauma) can also aid in determining if a subject is likely to have sepsis or in making a diagnosis of sepsis.

As used herein, "citrullated histone" refers to a histone in which at least one arginine has been converted to a citrulline, e.g., by enzymatic deamination/citrullation. In some embodiments, the histone can be an H3 or H4 histone. H3 family histone genes can include HIST1H3A (NCBI Gene ID: 8350); HIST1H3B (NCBI Gene ID: 8358); HIST1H3C (NCBI Gene ID: 8352); HIST1H3D (NCBI Gene ID: 8351); HIST1H3E (NCBI Gene ID: 8353); HIST1H3F (NCBI Gene ID: 8968); HIST1H3G (NCBI Gene ID: 8355); HIST1H3H (NCBI Gene ID: 8357); HIST1H3I (NCBI Gene ID: 8354); HIST1H3J (NCBI Gene ID: 8356); HIST2H3C (NCBI Gene ID: 126961); and HIST3H3 (NCBI Gene ID: 8290). H4 family histone genes can include HIST1H4A (NCBI Gene ID: 8359); HIST1H4B (NCBI Gene ID: 8366); HIST1H4C (NCBI Gene ID: 8364); HIST1H4D (NCBI Gene ID: 8360); HIST1H4E (NCBI Gene ID: 8367); HIST1H4F (NCBI Gene ID: 8361); HIST1H4G (NCBI Gene ID: 8369); HIST1H4H (NCBI Gene ID: 8365); HIST1H4I (NCBI Gene ID: 8294); HIST1H4J (NCBI Gene ID: 8363); HIST1H4K (NCBI Gene ID: 8362); HIST1H4L (NCBI Gene ID: 8368); and HIST4H4 (NCBI Gene ID: 121504).

Methods of measuring the level of a given histone or histone family are known in the art and can include, by way of non-limiting example Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluorescence assay; mass spectroscopy; FACS; and immunoelectrophoresis assay. Methods of measuring the level of citrullated histones are known in the art and can include, by way of non-limiting example western blotting with antibodies specific for citrullated forms of histones. In some embodiments, the level of a citrullated histone is the level of circulating citrullated histone, e.g. the level of citrullated histone in the subject's blood.

The methods described herein relate to the administration of inhibitors of citrullated histones. An inhibitor of citrullated histones can be any agent that decreases the level citrullated histones, whether by direct or indirect action. As used herein, the term "inhibitor" refers to an agent which reduces the level of the target by at least 10%, e.g. by 10% or more, 20% or more, 30% or more, 50% or more, 75% or more, 90% or more, 95% or more, 98% or more, or 99% or more. Inhibitors can be agents of any type and/or structure. The term "agent" refers generally to any entity which is normally not present or not present at the levels being administered to a cell, tissue or subject. An agent can be selected from a group comprising: polynucleotides; polypeptides; small molecules; antibodies; or functional fragments thereof. A polynucleotide can be RNA or DNA, and can be single or double stranded, and can be selected from a group comprising: nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid (DNA or RNA), small molecule, aptamer, protein, peptide, antibody, polypeptide comprising an epitope-binding fragment of an antibody, antibody fragment, peptide-nucleic acid (PNA), locked nucleic acid (LNA), small organic or inorganic molecules; saccharide; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or mammalian cells or tissues; naturally occurring or synthetic compositions; peptides; aptamers; and antibodies, or fragments thereof. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

In some embodiments, an inhibitor of citrullated histones can reduce and/or inhibit the citrullation of a histone, e.g., it can inhibit the activity of an enzyme that catalyzes the citrullation of a histone. In some embodiments, an inhibitor of citrullated histones can reduce the level of active and/or biologically-available citrullated histones, e.g., it can bind to citrullated histones, preventing their interaction with other proteins and/or DNA.

In some embodiments, the inhibitor of citrullated histones can be an inhibitor of protein citrullation, e.g. they reduce and/or inhibit the citrullation of proteins including histones. Examples of inhibitors of protein citrullation can include amidine-based inhibitors (e.g., Cl-amidine; F-amidine; biphenyl tetrazole tert-butyl Cl-amidine) and 1,2,3-triazole peptidomimetic-based inhibitors (e.g. compounds having the structures of 1-16 in the paragraph below). 1,2,3-triazole peptidomimetic-based inhibitors and their synthesis are described in the art, e.g., Trabocchi et al. J Enzyme Inhib Med Chem 2014 1-6; Bozdag et al. Bioorg Med Chem Lett 2013 23:715-9; and International Patent Publication WO/2011/098603; each of which is incorporated by reference herein in its entirety.

1-11

| | n | m | R |
|---|---|---|---|
| 1 | 1 | 1 | Ph |
| 2 | 1 | 1 | R) Ph |
| 3 | 1 | 1 | S) Ph |
| 4 | 3 | 1 | R) 4F—Ph |
| 5 | 3 | 1 | S) 4F—Ph |
| 6 | 3 | 1 | R) Ph |
| 7 | 3 | 1 | S) Ph |
| 8 | 2 | 1 | R) 4F—Ph |
| 9 | 2 | 1 | S) Ph |
| 10 | 3 | 1 | H |
| 11 | 1 | 2 | Ph |

12-15

| | o | m | R |
|---|---|---|---|
| 12 | 1 | 1 | R) Ph |
| 13 | 1 | 1 | S) Ph |
| 14 | 2 | 2 | R) Ph |
| 15 | 2 | 2 | S) Ph |

16

Peptidyl arginine deiminase (PAD) enzymes convert arginine residues to citrulline residues, e.g. it catalyzes the citrullation of histones. In some embodiments, the inhibitor of citrullated histones can be an inhibitor of a peptidyl arginine deiminase (PAD). In some embodiments, the PAD can be PAD4 (NCBI Gene ID: 23569). In some embodiments, the PAD can be PAD2 (NCBI Gene ID: 11240) Inhibitors of PAD can include, by way of non-limiting example Cl-amidine; F-amidine; YW3-56; o-F-amidine; 1,2,3-triazole peptidomimetic-based inhibitors; 2-chloroacetamidine (2CA); N-a-benzoyl-N5-(2 Chloro-1-iminoethyl)-L-Ornithine amide; ruthenium red; benzoyl-L-arginine amide (BAA); BA; BAEE; BAME; streptonigrin; ML325 and compounds having the structure of Formula I.

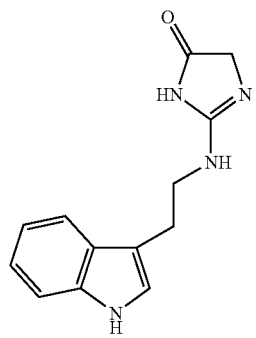

Formula I

Inhibitors of PAD and their synthesis are described in the art, e.g. in Ferretti et al. Med Chem Commun 2013 4:1109-1113; Teo et al. BMC Bioinformatics 2012 13:S4; Wang et al. J Biol Chem 2012 31:25941-53; Dreyton et al. Probe Reports from the NIH Molecular Libraries Program 2013; International Patent Publication WO2010/005293) each of which is incorporated by reference herein in its entirety.

In some embodiments, the inhibitor of citrullated histones can be an antibody reagent that specifically binds citrullated histones. In some embodiments, the antibody reagent specifically binds a citrullated histone and does not specifically bind the corresponding uncitrullated histone. As used herein, an "antibody reagent" encompasses polyclonal and monoclonal antibody preparations, as well as preparations including hybrid or chimeric antibodies, such as humanized antibodies, altered antibodies, $F(ab)_2$ fragments, F(ab) fragments, Fv fragments, single domain antibodies, dimeric and trimeric antibody fragment constructs, minibodies, and functional fragments thereof which exhibit immunological binding properties of the parent antibody molecule and/or which bind a cell surface antigen. Antibody reagents to specifically bind citrullated histones are known in the art, e.g., Product Nos. ab5103; ab19847; and ab80256 available from Abcam (Cambridge, Mass.).

The compositions and methods described herein can be administered to a subject having or diagnosed as having sepsis. In some embodiments, the methods described herein comprise administering an effective amount of compositions described herein, e.g. an inhibitor of citrullated histones to a subject in order to alleviate a symptom of sepsis. As used herein, "alleviating a symptom of sepsis" is ameliorating any condition or symptom associated with the sepsis. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, or injection administration. Administration can be local or systemic. In some embodiments, the compositions described herein, e.g. inhibitors of citrullated histones can be administered intravenously.

In some embodiments, the inhibitor of citrullated histones can be administered to a subject identified to have an elevated level of citrullated histones, e.g. an elevated level of citrullated H3 and/or H4 histones. In some embodiments, the level of citrullated histones is the level of circulating citrullated histones. In some embodiments, the methods described herein can further comprise the step of measuring the level of citrullated histones in a sample obtained from a subject prior to administering a treatment as described herein.

The term "effective amount" as used herein refers to the amount of, e.g., an inhibitor of citrullated histones needed to alleviate at least one or more symptom of the disease or disorder, and relates to a sufficient amount of pharmacological composition to provide the desired effect. The term "therapeutically effective amount" therefore refers to an amount of an inhibitor of citrullated histones that is sufficient to provide a particular anti-septic effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an inhibitor of citrullated histones which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for bacterial infection levels, among others. The dosage can be determined by a physician and adjusted, as necessary, to suit observed effects of the treatment.

In some embodiments, the technology described herein relates to a pharmaceutical composition comprising an inhibitor of citrullated histones as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. the inhibitor of citrullated histones as described herein.

In some embodiments, the pharmaceutical composition comprising an inhibitor of citrullated histones as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of inhibitors of citrullated histones as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an inhibitor of citrullated histones as disclosed herein can also be incorporated into the parenteral dosage forms of the disclosure, including conventional and controlled-release parenteral dosage forms.

Pharmaceutical compositions comprising an inhibitor of citrullated histones can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the inhibitor of citrullated histones can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. By way of non-limiting example, a subject can be administered an anti-infective, antibiotic, or antimicrobial. By way of further non-limiting example, if a subject is to be treated for inflammation according to the methods described herein, the subject can also be administered a second agent and/or treatment known to be beneficial for subjects suffering from inflammation. Examples of such agents and/or treatments include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; steroids, and the like.

In certain embodiments, an effective dose of a composition comprising an inhibitor of citrullated histones as described herein can be administered to a patient once. In certain embodiments, an effective dose of a composition comprising an inhibitor of citrullated histones can be administered to a patient repeatedly. For systemic administration, subjects can be administered a therapeutic amount of a composition comprising an inhibitor of citrullated histones such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. inflammation, bacterial counts, and/or citrullated histone levels by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the agent. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an inhibitor of citrullated histones can be administered over a period of time, such as over a 5 minute, 10 minute, 15 minute, 20 minute, or 25 minute period.

The dosage ranges for the administration of an inhibitor of citrullated histones, according to the methods described herein depend upon, for example, the form of the inhibitor, its potency, and the extent to which symptoms, markers, or indicators of a condition described herein are desired to be reduced, for example the percentage reduction desired for citrullated histone levels. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an inhibitor of citrullated histones in, e.g. the treatment of a condition described herein, or to induce a response as described herein (e.g. a reduction in sepsis) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. citrullated histone levels. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. citrullated histone levels and/or inflammation). It is well within the ability of one skilled in the art to monitor efficacy of administration and/or treatment by measuring any one of such parameters, or any combination of parameters. Efficacy can be assessed in animal models of a condition described herein, for example treatment of mouse models of sepsis. When using an experimental animal model, efficacy of treatment is evidenced when a statistically significant change in a marker is observed, e.g. citrullated histone levels, and/or bacterial counts.

In vitro and animal model assays are provided herein which allow the assessment of a given dose of an inhibitor of citrullated histones. By way of non-limiting example, the effects of a dose of an inhibitor of citrullated histones can be assessed by a murine CLP-induced sepsis model. A non-limiting example of a protocol for such an assay is as follows: the peritoneal cavity is opened under inhaled isoflurane anesthesia. Cecum is eviscerated, ligated below the ileocecal valve using a 5-0 suture, and punctured through and through (two holes) with a 20-gauge needle. The punctured cecum is squeezed to expel a small amount of fecal material and returned to the peritoneal cavity. The abdominal incision is closed in two layers with 4-0 silk suture. Sham-operated animals are handled in the same manner, except that the cecum is not ligated or punctured. The animals are then randomly divided into different groups for treatment with inhibitors of citrullated histones.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of sepsis. A subject can be male or female.

A subject can be one who has been previously diagnosed with or identified as suffering from or having a condition in need of treatment (e.g. sepsis) or one or more complications related to such a condition, and optionally, have already undergone treatment for sepsis or the one or more complications related to sepsis. Alternatively, a subject can also be one who has not been previously diagnosed as having sepsis or one or more complications related to sepsis. For example, a subject can be one who exhibits one or more risk factors for sepsis or one or more complications related to sepsis or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated." The terms "purified" or "substantially purified" refer to an isolated nucleic acid or polypeptide that is at least 95% by weight the subject nucleic acid or polypeptide, including, for example, at least 96%, at least 97%, at least 98%, at least 99% or more.

As used herein, "engineered" refers to the aspect of having been manipulated by the hand of man. For example, antibody reagent is considered to be "engineered" when the sequence of the antibody reagent is manipulated by the hand of man to differ from the sequence of an antibody as it exists in nature. As is common practice and is understood by those in the art, progeny and copies of an engineered polynucleotide and/or polypeptide are typically still referred to as "engineered" even though the actual manipulation was performed on a prior entity.

As used herein, an "epitope" can be formed on a polypeptide both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics.

"Avidity" is the measure of the strength of binding between an antigen-binding molecule (such as an antibody or antibody fragment thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant (KD of $10^{-5}$ to $10^{-12}$ moles/liter or less, such as $10^{-7}$ to $10^{-12}$ moles/liter or less, or $10^{-8}$ to $10^{-12}$ moles/liter (i.e., with an association constant (KA) of $10^5$ to $10^{12}$ liter/moles or more, such as $10^7$ to $10^{12}$ liter/moles or $10^8$ to $10^{12}$ liter/moles). Any KD value greater than $10^4$ mol/liter (or any KA value lower than $10^4$ $M^{-1}$) is generally considered to indicate non-specific binding. The KD for biological interactions which are considered meaningful (e.g., specific) are typically in the range of $10^{-10}$ M (0.1 nM) to $10^{-5}$ M (10000 nM). The stronger an interaction, the lower is its KD. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an peptide (e.g., an antibody reagent) described herein to bind to a target, such as a citrullated histone, with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. A polypeptide specifically bound to a target is not displaced by a non-similar competitor. In certain embodiments, an antibody reagent is said to specifically bind an antigen when it preferentially recognizes its target antigen in a complex mixture of proteins and/or macromolecules.

In some embodiments, an antibody reagent as described herein binds to a citrullated histone with a dissociation constant (KD) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, an antibody reagent as described herein binds to a citrullated histone with a dissociation constant (KD) of from about $10^{-5}$ M to $10^{-6}$ M. In some embodiments, an antibody reagent as described herein binds to a citrullated histone with a dissociation constant (KD) of from about $10^{-6}$ M to $10^{-7}$ M. In some embodiments, an antibody reagent as described herein binds to a citrullated histone with a dissociation constant (KD) of from about $10^{-7}$ M to $10^{-8}$ M. In some embodiments, an antibody reagent as described herein binds to a citrullated histone with a dissociation constant (KD) of from about $10^{-8}$ M to $10^{-9}$ M. In some embodiments, an antibody reagent as described herein binds to a citrullated histone with a dissociation constant (KD) of from about $10^{-9}$ M to $10^{-10}$ M. In some embodiments, an antibody reagent as described herein binds to a citrullated histone with a dissociation constant (KD) of from about $10^{-10}$ M to $10^{-11}$ M. In some embodiments, an antibody reagent as described herein binds to a citrullated histone with a dissociation constant (KD) of from about $10^{-11}$ M to $10^{-12}$ M. In some embodiments, an antibody reagent as described herein binds to a citrullated histone with a dissociation constant (KD) of less than $10^{-12}$ M.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies and single chains.

Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "CDR" refers to the complementarity determining regions within antibody variable sequences. There are three CDRs in each of the variable regions of the heavy chain and of the light chain, which are designated CDR1, CDR2 and CDR3, for each of the variable regions. The exact boundaries of these CDRs have been defined differently according to different systems. The system described by Kabat (Kabat et al., Sequences of Proteins of Immunological Interest (National Institutes of Health, Bethesda, Md. (1991)) not only provides an unambiguous residue numbering system applicable to any variable region of an antibody, but also provides precise residue boundaries defining the three CDRs. These CDRs may be referred to as Kabat CDRs. Other boundaries defining CDRs overlapping with the Kabat CDRs have been described by Padlan (FASEB J. 9:133-139 (1995)) and MacCallum (J Mol Biol 262(5):732-45 (1996)) and Chothia (J. Mol. Biol. 196:901-917 (1987) and Nature 342:877-883 (1989)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat defined CDRs.

The terms "antigen-binding fragment" or "antigen-binding portion" of an antibody, used interchangeably herein, refer to one or more fragments of an antibody as described herein, said fragments) still having the binding affinities as defined above herein. Fragments of a complete antibody have been shown to be able to carry out the antigen-binding function of an antibody. In accordance with the term "antigen-binding portion" of an antibody, examples of binding fragments include (i) an Fab fragment, i.e. a monovalent fragment composed of the VL, VH, CL and CH1 domains; (ii) an F(ab')2 fragment, i.e. a bivalent fragment comprising two Fab fragments linked to one another in the hinge region via a disulfide bridge; (iii) an Fd fragment composed of the VH and CH1 domains; (iv) an Fv fragment composed of the FL and VH domains of a single arm of an antibody; and (v) a dAb fragment consisting of a VH domain or of VH, CH1, CH2, DH3, or VH, CH2, CH3 (dAbs, or single domain antibodies, comprising only VL domains have also been shown to specifically bind to target epitopes). Although the two domains of the Fv fragment, namely VL and VH, are encoded by separate genes, they may further be linked to one another using a synthetic linker, e.g. a poly-G4S amino acid sequence (SEQ ID NO: 2), and recombinant methods, making it possible to prepare them as a single protein chain in which the VL and VH regions combine in order to form monovalent molecules (known as single chain Fv (ScFv). The term "antigen-binding portion" of an antibody is also intended to comprise such single chain antibodies. Other forms of single chain antibodies such as "diabodies" are likewise included here. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites (see, for example, Holliger, R, et al. (1993) Proc. Natl. Acad. Sci. USA 90:64446448; Poljak, R. J, et al. (1994) Structure 2:1121-1123). An immunoglobulin constant domain refers to a heavy or light chain constant domain. Human IgG heavy chain and light chain constant domain amino acid sequences are known in the art.

Furthermore, an antibody reagent as described herein may be part of a larger immunoadhesion molecule formed by covalent or noncovalent association of said antibody or antibody portion with one or more further proteins or peptides. Relevant to such immunoadhesion molecules are the use of the streptavidin core region in order to prepare a tetrameric scFv molecule (Kipriyanov, S. M., et al. (1995) Human Antibodies and Hybridomas 6:93-101) and the use of a cystein residue, a marker peptide and a C-terminal polyhistidinyl, e.g. hexahistidinyl tag (SEQ ID NO: 3) in order to produce bivalent and biotinylated scFv molecules (Kipriyanov, S. M., et al. (1994) Mol. Immunol. 31:10471058).

In some embodiments, the antibody reagent described herein can be an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding fragment thereof.

As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen (e.g. an epitope present on a cancer cell). Such conservatively modified variants are in addition to and do not exclude polymorphic variants, interspecies homologs, and alleles consistent with the disclosure.

In some embodiments, a conservatively modified variant of an antibody reagent can comprise alterations other than in the CDRs.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the antibody, antigen-binding portion thereof, and/or CAR as described herein can be a variant of a sequence described herein, e.g. a conservative substitution variant of an antibody polypeptide. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity, e.g. antigen-specific binding activity for the relevant target polypeptide, e.g. a cancer cell surface epitope. A wide variety of PCR-based site-specific mutagenesis approaches are also known in the art and can be applied by the ordinarily skilled artisan.

Examples of substitution variants include conservative substitution of amino acids, e.g. in a $V_H$ or $V_L$ domain, that do not alter the sequence of a CDR. A conservative substitution in a sequence not comprised by a CDR can be a substitution relative to a wild-type or naturally-occurring sequence, e.g. human or murine framework and/or constant regions of an antibody sequence.

A variant amino acid or DNA sequence preferably is at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by U.S. Pat. Nos. 4,518,584 and 4,737,462, which are herein incorporated by reference in their entireties.

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments, the antibody or antigen-binding portion thereof is a fully human antibody. In some embodiments, the antibody reagent is a humanized antibody or antibody reagent. In some embodiments, the antibody reagent is a chimeric antibody reagent. In some embodiments, the antibody reagent is a recombinant polypeptide.

The term "human antibody" refers to antibodies whose variable and constant regions correspond to or are derived from immunoglobulin sequences of the human germ line, as described, for example, by Kabat et al. (see Kabat, et al. (1991) Sequences of Proteins of Immunological Interest, Fifth Edition, U.S. Department of Health and Human Services, NIH Publication No. 91-3242). However, the human antibodies can contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies as described herein have variable regions and may also contain constant regions derived from immunoglobulin sequences of the human germ line (see Kabat, E. A., et al. (1991) Sequences of Proteins of Immunological Interest, Fifth Edition, U.S. Department of Health and Human Services, NIH Publication No. 91-3242). According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody.

The term "chimeric antibody" refers to antibodies which contain sequences for the variable region of the heavy and light chains from one species and constant region sequences from another species, such as antibodies having murine heavy and light chain variable regions linked to human constant regions. Humanized antibodies have variable region framework residues substantially from a human antibody (termed an acceptor antibody) and complementarity determining regions substantially from a non-human antibody, e.g. a mouse-antibody, (referred to as the donor immunoglobulin). See, WO 90/07861, U.S. Pat. No. 5,693, 762, U.S. Pat. No. 5,693,761, U.S. Pat. No. 5,585,089, U.S. Pat. No. 5,530,101 and Winter, U.S. Pat. No. 5,225,539, which are herein incorporated by reference in their entirety. The constant region(s), if present, are also substantially or entirely from a human immunoglobulin. The human variable domains are usually chosen from human antibodies whose framework sequences exhibit a high degree of sequence identity with the (murine) variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies. See Carter et al., WO 92/22653, which is herein incorporated by reference in its entirety.

As used herein, the term "humanized antibody" refers to an antibody (or antigen-binding portion thereof) comprising a human framework, at least one complementarity determining regions (CDR) from a non-human antibody, and in which any constant region present is substantially identical to a human immunoglobulin constant region, i.e., at least about 85-90%, preferably at least 95% identical. Hence, all parts of a humanized immunoglobulin, except possibly the CDRs, are substantially identical to corresponding parts of one or more native human immunoglobulin sequences.

In some embodiments, the antibody reagents described herein are not naturally-occurring biomolecules. For example, a murine antibody raised against an antigen of human origin would not occur in nature absent human intervention and manipulation, e.g. manufacturing steps carried out by a human. Chimeric antibodies are also not naturally-occurring biomolecules, e.g., in that they comprise sequences obtained from multiple species and assembled into a recombinant molecule. In certain particular embodiments, the human antibody reagents described herein are not naturally-occurring biomolecules, e.g., fully human antibodies directed against a human antigen would be subject to negative selection in nature and are not naturally found in the human body.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives for hybridoma-based production systems. The main advantages of transgenic animals are potential high yields from renewable sources.

Nucleic acid molecules encoding amino acid sequence variants of antibodies are prepared by a variety of methods known in the art. These methods include, but are not limited to preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations can be used to construct nucleic acid sequences which encode a monoclonal antibody molecule, antigen binding region thereof, or CAR.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art.

Accordingly, the expression of an antibody, antigen-binding portion thereof, or CAR as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or portion thereof as described herein with a specified amino terminus sequence. Moreover, problems associated with retention of initiation codon-derived methionine residues in direct yeast (or bacterial) expression maybe avoided. Any of a series of yeast gene expression systems incorporating promoter and termination elements from the actively expressed genes coding for glycolytic enzymes produced in large quantities when yeast are grown in mediums rich in glucose can be utilized to obtain recombinant antibodies, antigen-binding portions thereof, or CARs thereof as described herein. Known glycolytic genes can also provide very efficient transcriptional control signals. For example, the promoter and terminator signals of the phosphoglycerate kinase gene can be utilized.

Production of antibody reagents as described herein in insects can be achieved. For example, by infecting the insect host with a baculovirus engineered to express a transmembrane polypeptide by methods known to those of ordinary skill in the art.

In some embodiments, the introduced nucleotide sequence is incorporated into a plasmid or viral vector capable of autonomous replication in the recipient host. Any of a wide variety of vectors can be employed for this purpose and are known and available to those or ordinary skill in the art. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli*, for example. Other gene expression elements useful for the expression of cDNA encoding antibodies, antigen-binding portions thereof, or CARs include, but are not limited to (a) viral transcription promoters and their enhancer elements, such as the SV40 early promoter, Rous sarcoma virus LTR, and Moloney murine leukemia virus LTR; (b) splice regions and polyadenylation sites such as those derived from the SV40 late region, and (c) polyadenylation sites such as in SV40. Immunoglobulin cDNA genes can be expressed as described, e.g., using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA, the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric immunoglobulin chain gene product are then transfected singly with an antibody reagent. The transfected recipient cells are cultured under conditions that permit expression of the incorporated genes and the expressed immunoglobulin chains or intact antibodies or fragments are recovered from the culture.

In some embodiments, the fused genes encoding the antibody reagent, or portions thereof are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes. Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the fused genes encoding chimeric H and L chains can be assembled on the same expression vector.

For transfection of the expression vectors and production of the chimeric, humanized, or composite human antibodies described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a chimeric, humanized, or composite human antibody construct, and/or antibody reagent as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment.

In some aspects, provided herein are methods and systems for the production of a humanized antibody, which is prepared by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors can be the same vector. Also provided herein are DNA sequences encoding the light chain or the heavy chain of the humanized antibody; an expression vector that incorporates a said DNA sequence; and a host transformed with a said expression vector.

Usually the CDR regions in humanized antibodies and human antibody variants are substantially identical, and more usually, identical to the corresponding CDR regions in the mouse or human antibody from which they were derived. Although not usually desirable, it is sometimes possible to make one or more conservative amino acid substitutions of CDR residues without appreciably affecting the binding affinity of the resulting humanized immunoglobulin or human antibody variant. Occasionally, substitutions of CDR regions can enhance binding affinity.

In addition, techniques developed for the production of "chimeric antibodies" by splicing genes from a mouse, or other species, antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region, e.g., humanized antibodies.

The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells (WO 87/02671; which is incorporated by reference herein in its entirety). The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with an antibody reagent as described herein. Such functional activities include binding to cancer cells and/or anti-cancer activity. Additionally, a polypeptide having functional activity means the polypeptide exhibits activity similar, but not necessarily identical to, an activity of a reference antibody reagent as described herein, including mature forms, as measured in a particular assay, such as, for example, a biological assay, with or without dose dependency. In the case where dose dependency does exist, it need not be identical to that of the reference antibody reagent, but rather substantially similar to the dose-dependence in a given activity as compared to the reference antibody reagent as described herein (i.e., the candidate polypeptide will exhibit greater activity, or not more than about 25-fold less, about 10-fold less, or about 3-fold less activity relative to the antibody reagents described herein).

As used herein, the terms "treat" "treatment" "treating," or "amelioration" refer to therapeutic treatments, wherein the object is to reverse, alleviate, ameliorate, inhibit, slow down or stop the progression or severity of a condition associated with a disease or disorder, e.g. sepsis. The term "treating" includes reducing or alleviating at least one adverse effect or symptom of a condition, disease or disorder associated with sepsis. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method for treating one or both of sepsis and septic shock in an individual, comprising:
   identifying an individual having sepsis; and
   administering to the individual at least one agent that inhibits production of citrullinated histone H3 (Cit H3) in the individual.
2. The method of paragraph 1 wherein the least one agent is an inhibitor of histone deacetylase.
3. The method of paragraph 1 wherein least one agent is an inhibitor of peptidylarginine deiminase.
4. The method of paragraph 2 wherein the inhibitor is suberoylanilide hydroxamic acid.
5. The method of paragraph 3 wherein the inhibitor is Cl-amidine.
6. A method for treating one or both of sepsis and septic shock in an individual, comprising:
   identifying an individual having sepsis; and
   administering to the individual least one agent that neutralizes circulating citrullinated histone H3 in the individual.
7. The method of paragraph 6 wherein the least one agent is an antibody.
8. The method of paragraph 7 wherein the antibody is an anti-Cit H3 antibody.

Some embodiments of the technology described herein can be defined according to any of the following numbered paragraphs:

1. A method of treating sepsis and/or septic shock in a subject in need thereof, the method comprising administering a therapeutically effective amount of an inhibitor of citrullated histones to the subject.
2. The method of paragraph 1, wherein the inhibitor of citrullated histones is an inhibitor of protein citrullation.

3. The method of paragraph 1, wherein the inhibitor of citrullated histones is an inhibitor of a peptidyl arginine dehninase (PAD).
4. The method of paragraph 4, wherein the PAD is selected from the group consisting of: PAD2 and PAD4.
5. The method of any of paragraphs 2-4, wherein the inhibitor of protein citrullation is selected from the group consisting of:
   amidine-based inhibitors; Cl-amidine; F-amidine; biphenyl tetrazole tert-butyl Cl-amidine; YW3-56; o-F-amidine; 1,2,3-triazole peptidomimetic-based inhibitors; 2-chloroacetamidine (2CA); N-a-benzoyl-N5-(2 Chloro-1-iminoethyl)-L-Ornithine amide; ruthenium red; benzoyl-L-arginine amide (BAA); BA; BAEE; BAME; streptonigrin; and ML325.
6. The method of paragraph 1, wherein the inhibitor of citrullated histones is an antibody reagent that specifically binds citrullated histones.
7. The method of paragraph 6, wherein the antibody reagent specifically binds a citrullated histone and does not specifically bind the corresponding uncitrullated histone.
8. The method of any of paragraphs 1-7, wherein the citrullated histone is citrullated H3 or citrullated H4.
9. The method of any of paragraphs 1-8, wherein the level of a citrullated histone is the level of circulating citrullated histone.
10. The method of any of paragraphs 1-9, wherein the administration is intravenous.
11. The method of any of paragraphs 1-10, wherein the subject is a subject identified to have an elevated level of citrullated histone.

EXAMPLES

Example 1

In a rodent model of lipopolysaccharide (LPS)-induced shock, an increase in blood citrullinated histone H3 (Cit H3) is associated with lethality of sepsis, and treatment with suberoylanilide hydroxamic acid (SAHA), a histone deacetylase (HDAC) inhibitor (HDACI), significantly improves survival. However, the role of Cit H3 in pathogenesis and therapeutics of sepsis are largely unknown. Described herein is whether the HDACI could inhibit cellular Cit H3 production, and inhibition of peptidyalgrinine deiminase (PED, an enzyme producing Cit H3) with Cl-amidine (PAD inhibitor) or neutralization of blood Cit H3 with anti-Cit H3 antibody could improve survival in a clinically relevant mouse model of cecal ligation and puncture (CLP) induced septic shock.

Three experiments were carried out. In experiment I, HL-60 neutrophilic cells grown on a coverslip were treated with LPS (100 ng/ml) in the presence or absence of SAHA (5 limo]) for 3 h, and subjected to immuno-staining with anti-Cit H3 antibody to assess effect of SAHA on Cit H3 production under a fluorescence microscope. The ratio of Cit H3 positive cells was calculated as mean±SD (n=3). In experiment II, male C57BL/6J mice were subjected to CLP, and 1 hour later randomly divided into three groups for intraperitoneal injection as follows: (1) dimethyl sulfoxide (DMSO), (2) SAHA (50 mg/kg) in DMSO, and (3) Cl-amidine (40 mg/kg) in DMSO (n=10/group). In a separate experiment III, the male C57BL/6J mice were divided into control and treatment groups, and subjected to CLP. One hour later, immunoglobulin (IgG) and Cit H3 antibody (20 mg/kg iv; n=5/group) were injected into the control and treatment groups, respectively. All survival was monitored for 5-10 days.

Figure 2:
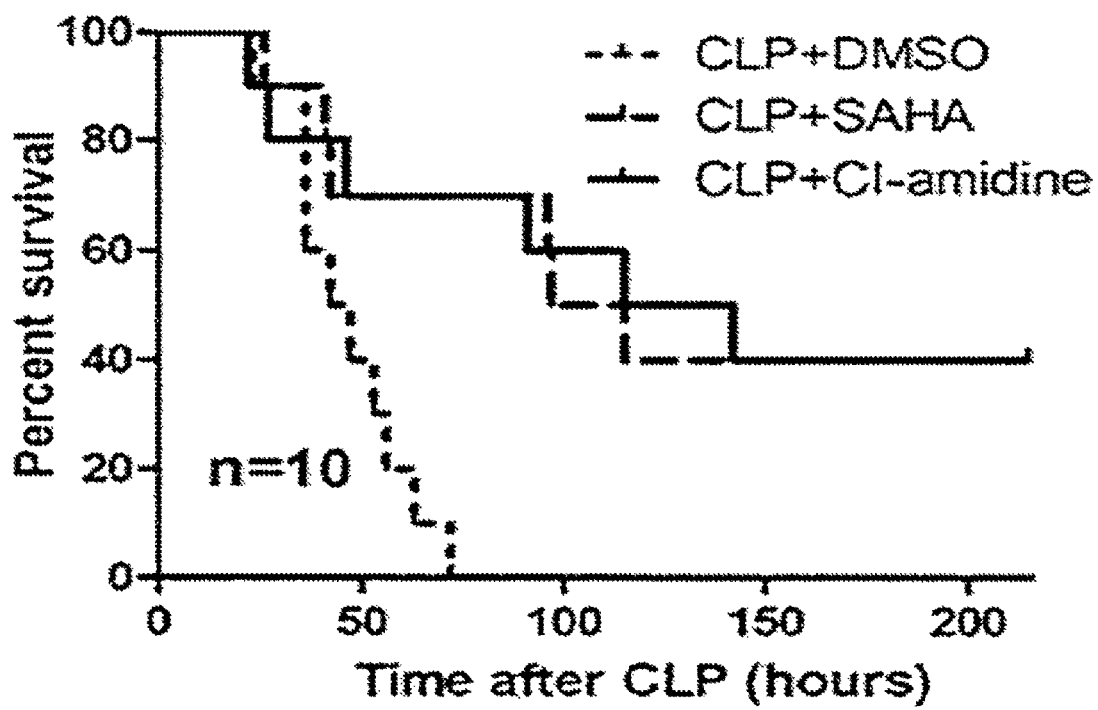
FIG. 2 demonstrates that Cl-amidine protects mice against sepsis-caused lethality. Mice were intraperitoneally administered 80 mg/kg of Cl-amidine or vehicle DMSO 1 h after CLP (n=10). SAHA treated animal (50 mg/kg) served as a positive control. Survival was monitored for 10 days. Treatment with Cl-amidine significantly improved survival compared with DMSO vehicle group (42.5% versus 0% survival; P<0.001)
Figure 3:
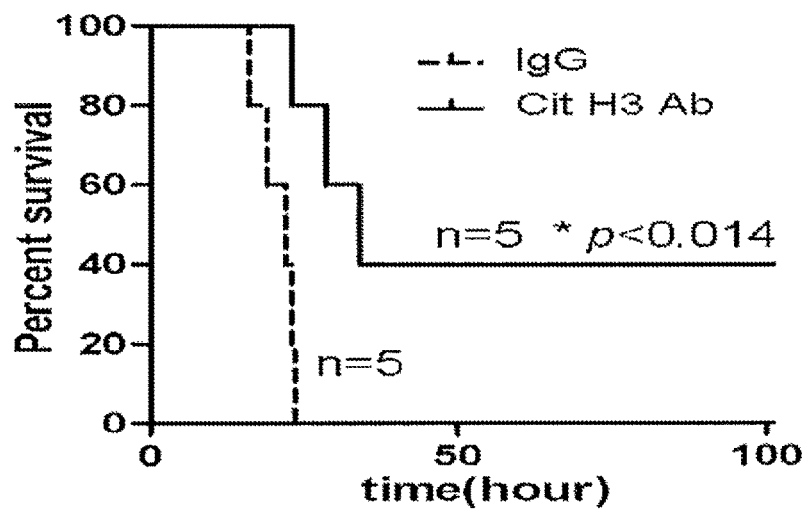
FIG. 3 demonstrates that neutralization of blood Cit H3 with anti-Cit H3 antibody improves survival in a mouse model of CLP-induced sepsis. Mice were intravenously administrated with the purified anti-Citrullinated H3 antibody (20 mg/kg) or immunoglobulin G (Ig G, 20 mg/kg) 2 h after CLP (n=5/group). Survival was monitored for 5 days. Treatment with the antibody against Cit H3 significantly improved survival compared to Ig G group (42% versus 9% survival, P<0.014).

In experiment I, LPS induced Cit 1h3 production in the HL-60 cells, while SAHA treatment inhibited H3 citrullination significantly (FIG. 1). In an in vivo study of experiment II, all vehicle injected mice died within 3 days with increased blood Cit H3, whereas treatment with the HDACI or Cl-amidine notably improved long term survival (FIG. 2, $p<0.004$). In experiment III, IgG did not prolong animal life, but treatment with Cit H3 specific antibody, even only once, significantly improved survival (FIG. 3, $p<0.014$).

Inhibition of HDAC or PAD significantly suppresses Cit H3 production in vitro and improves survival in vivo, Neutralization of blood Cit H3 remarkably prolongs life of septic mice. Collectively, the results described herein demonstrate that Cit H3 is not only a biomarker but also a novel therapeutic target for sepsis.

Septic shock is a lethal complication of infection, characterized by dysregulated inflammatory and immune responses. Epigenetic mechanisms such as post-translational modification (PTM) of histones by acetylation are master regulators of gene expression and play a critical role in inflammatory and host defense responses.[1,2] Histone acetylation is controlled by histone acetyltransferases (HAT) and histone deacetylases (HDAC), which affect expression of genes and proteins involved in various key cellular functions.[3,4] Numerous HDAC inhibitors (HDACI) are already in use for the treatment of cancers[5,6]. An HDACI, suberoylanilide hydroxamic acid (SAHA), modulates the immune response,[7-9] and improves survival in a mouse model of cecal ligation and puncture (CLP).[10]

Citrullination of histones is another PTM catalyzed by peptidylarginine deiminase (PAD)-4 (PAD4). Citrullinated histone H3 (Cit H3) could be a potential serum biomarker for the early diagnosis of septic shock[14] Described herein is the determination of whether Cit H3 is a therapeutic target for sepsis and/or septic shock.

Described herein is the determination of whether treatment with HDACI can inhibit Cit H3 production. In addition, it was investigated whether inhibition of peptidyalargi nine deiminase with Cl-amidine, a pan-PAD inhibitor, or neutralization of circulating Cit H3 with anti-Cit H3 antibody would improve survival in a mouse model of cecal ligation and puncture (CLP).

Materials and Methods

Antibodies and supplies. LPS (from *S. typhosa*, Cat# L6386, Lot#038k4005) and dimethyl sulfoxide (DMSO) were purchased from the Sigma Aldrich, Co (St. Louis, Mo.). Suberoylanilide hydroxamic acid was purchased from Enzo Life Sciences International, Inc (Plymouth Meeting, Pa.). Cl-amidine was purchased from Cayman Chemical (Ann Arbor, Mich.). Purified citrullinated histone H3 (citrulline 2+8+17) antibody and immunoglobulin G (Ig G, ab171870; control for the antibody) were purchased from abcam (Cambridge, Mass.). RPMI 1640 medium, fetal bovine serum (FBS), and phosphate buffered saline (PBS) were from Gibco-BRL (Grand Island, N.Y.). L-glutamine, and fetal calf serum (FCS) were from Invitrogen (Carlsbad, Calif.). All-trans retinoic acid (ATRA) was purchased from Acros Organics (Geel, Belgium). All other chemicals in this study were of analytical grade and obtained from the Sigma-Aldrich unless mentioned otherwise.

Cell culture and treatment. HL-60 cells obtained from American Type Culture Collection (ATCC) were maintained in Iscove's modified DMEM medium (Invitrogen Life Technologies, Carlsbad, Calif.) supplemented with 20% fetal bovine serum (FBS). These cells were grown on a coverslip at 37° C. in a humidified incubator in 5% CO2 and 95% air, and were differentiated into granulocytes by culturing the cells in medium containing 1 µM ATRA for 3 days. The ATRA-differentiated HL-60 granulocytes were treated with 4 µM calcium ionophore in medium containing 1.5 mM calcium chloride, and then incubated with LPS (100 ng/ml) in the presence or absence of SAHA (10 pM) over 3 h. Following incubation, medium was collected, cells were fixed and subjected to immunostaining with anti-Cit H3 antibody following by the second antibody. The ratio of Cit H3 positive stained cells to all cells was counted and calculated as mean±SD from three individual experiments.

Animals. Male C57B1/6J mice (6-8 weeks) weighing 25-30 g were purchased from Jackson Labs (Bar Harbor, Me.). All animals were housed in plastic cages and had access to chow and water throughout the experiment. They were kept at room temperature (24±2° C.) and exposed to alternative cycles of 12 h light and darkness. During the experiments the animals were monitored up to 10 days, and survival rate was compared between the experimental and control groups.

CLP-induced sepsis model. The CLP murine model,[15] modified as described previously, was used to induce fecal peritonitis.[16] In brief, peritoneal cavity was opened under inhaled isoflurane anesthesia. Cecum was eviscerated, ligated below the ileocecal valve using a 5-0 suture, and punctured through and through (two holes) with a 20-gauge needle. The punctured cecum was squeezed to expel a small amount of fecal material and returned to the peritoneal cavity. The abdominal incision was closed in two layers with 4-0 silk suture Animals were resuscitated by subcutaneous injection of 1 mL of saline. Sham-operated animals were handled in the same manner, except that the cecum was not ligated or punctured. The animals were then randomly divided into different groups for two separate in vivo experiments as follows.

Administration of inhibitors and experimental design. In one of the survival experiments, mice received intra-peritoneal SAHA (HDAC inhibitor, 50 mg/kg)[10] or Cl-amidine (PAD inhibitor, 80 mg/kg)[16] dissolved in dimethyl sulfoxide (DMSO), or vehicle DMSO 1 hour after CLP (n=10/group). Mortality was recorded for up to 10 days post procedure.

Administration of antibody and experimental design. In the other survival experiment, mice received intravenous anti-Cit H3 antibody (20 mg/kg; abcam, Cambridge, Mass.) or immunoglobulin G (20 mg/kg; EMD Millipore, Billerica, Mass.) 2 hours after CLP (n=5/group). Mortality was recorded for up to 5 days.

Statistical analysis. Statistical differences were determined by Student t tests and ANOVA for two group and multiple group comparisons respectively (SPSS™ statistical software package, Chicago, Ill.). Kaplan-Meier survival curves were analyzed by using the MedCalc™ Statistical Software (Mariakerke, Belgium) for the in vivo studies. Differences were considered to be statistically significant when p values were <0.05.

Results

SAHA Suppresses LPS-Induced ET Formation.

LPS stimulates histone H3 citrullination and NETs formation, which in turn releases nuclear content (e.g., histones) into the extracellular milieu. Therefore, it was asked whether SAHA treatment could attenuate these alterations. As expected, LPS induced citrullination of H3, which spilled out of the cell during the formation of NETs (data not shown). SAHA treatment significantly inhibited histone H3 citrullination and NETs formation in HL-60 neutrophilic cells after LPS insult (FIG. 1B).

Inhibition of PAD with Cl-Amidine Improves Survival in a Mouse Model of CLP-Induced Septic Shock.

To assess if decreased Cit H3 production could protect against lethality, Cl-amidine (80 mg/kg, i.p.), a PAD inhibitor (PAM), was injected into mice 1 hour after CLP. As a positive control, mice were given SAHA (50 mg/kg, i.p.). All the mice from the vehicle control group died within 3 days. Treatment with Cl-amidine significantly improved survival (p<0.01), similar to SAHA (FIG. 2).

Neutralization of Circulating Cit h3 with Anti-Cit H3 Antibody Improves Survival in a Mouse Model of CLP-Induced Septic Shock.

To determine whether blockade of Cit H3 activity could prolong survival, anti-Cit H3 antibody was intravenously injected 2 hours after CLP. Mouse immunoglobulin G was used as a control (n=5/group). As shown in FIG. 3, all of the animals that received IgG died within 3 days. In contrast, antibody treated animals showed a significant improvement in survival (p<0.014).

Discussion

Treatment of septic mice with SAHA, a potent histone deacetylase inhibitor, improves survival.[7,14,20] Described herein is the demonstration that LPS-induced histone H3 citrullination can be attenuated in vitro by SAHA treatment. In addition, a decrease in Cit H3 levels (through an inhibition of the PAD4 enzyme), or blockage of its actions (by specific antibody) improves survival in a lethal CLP model.

Epigenetic mechanisms and, in particular, the PTM of histones can contribute to the unbalanced inflammatory and immune status that is often seen in the advanced stages of sepsis. Among the dozens of possible histone PTMs, it is demonstrated herein that citrullination of arginines on the N-terminal tail of histone H3 exhibits a particularly strong link with sepsis, and can be a therapeutic target. First, the HDAC inhibitor SAHA while increasing the acetylation of histone proteins, decreases their citrullination[7]. Second, an inhibition of PAD activity with Cl-amidine can reduce the production of Cit H3 (data not shown) and improve survival in the CLP model. Third, neutralization of circulating Cit H3 with anti-Cit H3 antibody significantly decreases the lethality of this model. The data presented herein indicate that circulating levels of Cit H3 play a key regulatory role in the pathogenesis of sepsis.

Citrullination, also termed deamination, is a post-translational protein modification that leads to a charge loss that can alter its conformation and consequently its structure, function and interaction with other proteins. This PTM is catalyzed by the Ca2+-dependent peptidyl arginine deiminases (PADS). There are five PAD family members, but only PAD2 and PAD4 expression are closely linked with inflammatory diseases such as rheumatoid arthritis (RA).[21,22] While PAD2 is broadly expressed across tissue types, including immune cells, expression of PAD4 is restricted to immune cells, in particular macrophages and granulocytes.[21,23,24]

Without wishing to be limited by theory, it is contemplated herein that rapid and robust histone citrullination can lead to the death of cells such as neutrophils, which are the initial responders during sepsis. Following their release from the disintegrated neutrophils, citrullinated histones bind to and activate TLR2/4, creating a positive feedback loop that results in the release of additional Cit H3, establishing a vicious circle. The finding that hyper-citrullinated histone H3 can be detected in the early stages of sepsis and is associated with lethality supports this possibility.

CI-amidine, a recently described pan-PAD inhibitor, has been used as a potent PAD4 inhibitor. Treatment with CI-amidine can reduce the severity of murine collagen-induced arthritis. Intriguingly, it is demonstrated herein that this inhibitor can also improve survival in a model of lethal CLP-sepsis. Although the mechanisms are not entirely clear, this demonstrates that inhibition of PAD4 can serve as a target for future development of novel drugs for the treatment of sepsis.

Figure 4A:
FIG. 4A depicts a schematic drawing of the N-terminal tail of histone 113 showing that arginines 2 (R2), 8 (R8), 17 (R17), and 26 (R26) are the substrates of peptidyl arginine dehninase (PAD), and that lysines 4 (K4), 9 (K9), 14, (K14), 18 (K18), 23 (K23), and 27 (K27) are the substrates of histone acetyl transferase (HAT)/histone deacetylase (HDAC). Figure discloses SEQ ID NO: 1.
Figure 4B:
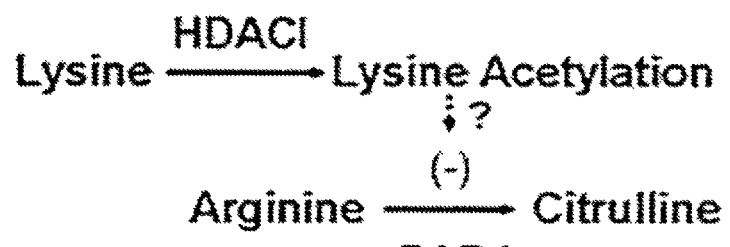
FIG. 4B demonstrates a model in which, due to amino acids of lysine and arginine are close to each other, increase in lysine acetylation by HDACI can suppress arginine citrullination by PAD.

The relationship between histone acetylation and citrullination is unclear. Post-translational histone modifications are thought to regulate gene expression by facilitating the formation of open chromatin or serving as binding platform for additional effector proteins.[28,29] Given that the arginine and lysine side chains on the N-terminal tail of histone H3, which have previously been identified as sites of citrullination and acetylation,[29] are directly adjacent or in close vicinity, PTMs of the respective lysine side chains by acetylation or methylation can potentially alter the recognition motif of chromatin modifying enzymes that process adjacent amino acid residues (FIGS. 4A-4B)[30,31] Arginine residues often play a central role in the structural integrity of a protein, due to their ability to participate in ionic interactions with negatively charged amino acid side chains, substrates, and cofactors, and to form multiple hydrogen bonds with the peptide backbone and other amino acid side chains.[32] Arginine also has the most polar of all the common amino acid side chains and is therefore the amino acid that is most likely to be found on the surface of the proteins in an aqueous environment.[32] Citrullination would be expected to destroy the ionic interactions, interfere with hydrogen bonds, and create new interactions. Hence, the conversion of arginine into citrulline may result in an altered three-dimensional structure and function of the protein.[33] Similarly, lysine acetylation in histones is generally believed to allow chromatin to assume a more open state, permitting transcriptional activity. Treatment of immune cells or animals with HDACI strongly inhibits proinflammatory cytokines.[3,7] It is conceivable that binding of an effector protein to a specific site on the histone can prevent another PTM protein from binding the same histone. In summary, using a combination of in vitro and in vivo experiments, it is demonstrated herein that blockage of Cit H3 can be protective against lethality due to sepsis.

REFERENCES

1. Roger T, Lugrin J, Le Roy D, Goy G, Mombelli M, Koessler T, Ding X C, Chanson A L, Reymond M K, Miconnet I, Schrenzel J, Francois P, Calandra T. Histone deacetylase inhibitors impair innate immune responses to Toll-like receptor agonists and to infection. Blood. 2011; 117(4): 1205-1217.
2. Ciarlo E, Savva A, Roger T. Epigenetics in sepsis: targeting histone deacetylases. Int J Antimicrob Agents. 2013; 42 Suppl: S8-12.
3. Leoni F Z A, Bertolini G, Porro G, Pagani P, Pozzi P, Dona G, Fossati G, Sozzani S, Azam T, Buffer P, Fantuzzi G, Goncharov I, Kim S H, Pomerantz B J, Reznikov L L, Siegmund B, Dinarello C A, Mascagni P: The antitumor histone deacetylase inhibitor suberoylanilide hydroxamic acid exhibits antiinflammatory properties via suppression of cytokines. Proc Natl Acad Sci U.S.A. 99: 2995-3000, 2002.
4. Li Y, Liu B, Gu X, Kochanek A R, Fukudome E Y, Liu Z, Zhao T, Chong W, Zhao Y, Zhang D, Libermann T A, Alani H B. Creating a "pro-survival" phenotype through epigenetic modulation. Surgery. 2012; 152(3): 455-464.
5. Butler L M, Zhou X, Xu W S, Scher H I, Rifkind R A, Marks P A, Richon V M. The histone deacetylase inhibitor SAHA arrests cancer cell growth, up-regulates thioredoxin-binding protein-2, and down-regulates thioredoxin. Proc Natl Acad Sci USA. 2002; 99(18): 11700-11705.
6. Marks P A, Jiang X, Histone deacetylase inhibitors in programmed cell death and cancer therapy. Cell Cycle. 2005; 4(4): 549-551.
7. Li Y, Liu B, Zhao H, Sailhamer E A, Fukudome E Y, Zhang X, Kheirbek T, Finkelstein R A, Velmahos G C, deMoya M, Hales C A, Alam H B. Protective effect of suberoylanilide hydroxamic acid against LPS-induced septic shock in rodents. Shock. 2009; 32(5):517-523.
8. Chong W, Li Y, Lin B, Zhao T, Fukudome E Y, Liu Z, Smith W M, Velmahos G C, deMoya M A, Alam I I B. Histone deacetylase inhibitor suberoylanilide hydroxamic acid attenuates Toll-like receptor 4 signaling in lipopolysaccharide-stimulated mouse macrophages, J Surg Res. 2012; 178(2); 851-859.
9. Chong W, Li Y, Liu B, Liu Z, Zhao T, Wonsey D R, Chen C, Velmahos G C, deMoya M A, King D R, Kung A L, Alam H B. Anti-inflammatory properties of histone deacetylase inhibitors: a mechanistic study. J Trauma Acute Care Surg, 2012; 72(2):347-353; discussion 353-354.
10. Zhao T, Li Y, Liu B, Liu Z, Chong W, Duan X, Deperalta D K, Velmahos G C, Alain H B, Novel pharmacologic treatment attenuates septic shock and improves long-term survival. Surgery. 2013; 154(2): 206-213.
11. Neeli, I., Khan, S. N. & Radic, M. Histone deitnination as a response to inflammatory stimuli in neutrophils. J Immunol 2008; 180: 1895-1902.
12. Guimaraes-Costa, A. B., Nascimento, M. T., Wardini, A. B., Pinto-da-Silva, L, H. & Saraiva, E. M. ETosis: A Mierobicidal Mechanism beyond Cell Death. J Parasitol Res 2012; 2012, 929743.
13. Goldinann, 0., Medina, E. The expanding world of extracellular traps: not only neutrophils but much more. Front Iinmunol 2012; 3: 420.
14. Li, Y., Liu, B., Fukudome, E. Y., Lu, J., Chong, W., Jin, G., Liu, Z., Velmahos, G. C., Demoya, M., King, D. R., Alain, H. B. Identification of citrullinated histone H3 as a potential serum protein biomarker in a lethal model of lipopolysaccharide-induced shock. Surgery 2011; 150: 442-451.
15. Rittirsch D, Huber-Lang M S, Flier! M A, Ward P A Immunodesign of experimental sepsis by cecal ligation and puncture. Nat Protoc 2009; 4:31-36,
16. Lange S, Gogel S, Leung K Y, Vernay B, Nicholas A P, Causey C P, Thompson P R, Greene N D, Ferretti P. Protein deiminases: new players in the developmentally regulated loss of neural regenerative ability. Dcv Biol. 2011; 355(2): 205-214.
17. Neeli I, Dwivedi N, Khan S, Radic M. Regulation of extracellular chromatin release from neutrophils. J Innate Immun. 2009; 1(3):194-201,
18. Wang Y, Li M, Stadler S, Correll S, Li P, Wang D, Hayama R, Leonelli L, Han H, Grigoryev S A, Allis C D, Coonrod S A. Histone hypercitrullination mediates chromatin decondensation and neutrophil extracellular trap formation. J Cell Biol. 2009; 184(2): 205-213.
19. Kan R, Jin M, Subramanian V, Causey C P, Thompson P R, Coonrod S A. Potential role for PADI-mediated histone citrullination in preimplantation development. BMC Dew Biol. 2012; 12:19.
20. Li Y, Liu B, Fukudome E Y, Kochanek A R, Finkelstein R A, Chong W, Jin G, Lu J, deMoya M A, Velinahos G C, Alam H B. Surviving lethal septic shock without fluid resuscitation in a rodent model. Surgery. 2010; 148(2): 246-254.
21. Foulquier C, Sebbag M, Clavel C, Chapuy-Regaud S, Al Badine R, Mechin M C, Vincent C, Nachat R, Yamada M, Takahara H, Simon M, Guertin M, Serre G: Peptidyl arginine deiminase type 2 (PAD-2) and PAD-4 but not PAD-1, PAD-3, and PAD-6 are expressed in rheumatoid arthritis synovium in close association with tissue inflammation. Arthritis Rheum 2007; 56:3541-3553,
22. Vossenaar E R, Radstake T R, van der Heijden A, van Mansum M A, Dieteren C, de Rooij D J, Barrera P, Zendman A J, van Venrooij W J: Expression and activity of citrullinating peptidylarginine deiminase enzymes in monocytes and macrophages. Ann Rheum Dis 2004; 63:373-381.
23. Asaga H, Nakashima K, Senshu T, Ishigami A, Yamada M: Immunocytochemical localization of peptidylarginine deiminase in human eosinophils and neutrophils. J Leukoc Biol 2001; 70:46-51,
24. Rohrbach A S, Hemmers S, Arandjelovic S, Con. M, Mowen K A. PAD4 is not essential for disease in the K/BxN murine autoantibody-mediated model of arthritis. Arthritis Res Thor. 2012; 14(3): R104.
25. Brinkmann V, Reichard U, Goosmann C, Fauler B, Uhlmann Y, Weiss D, Weinrauch Y, Zychlinsky A. Neutrophil Extracellular Traps Kill Bacteria. Science 2004; 303: 1532-1535.
26. Slack J L, Causey C P, Thompson P R, Protein arginine deiminase 4: a target for an epigenetic cancer therapy. Cell Mol Life Sci. 2011; 68(4): 709-720.
27. Willis V C, Gizinski A M, Banda N K, Causey C P, Knuckley B, Cordova K N, Luo Y, Levitt B, Glogowska M, Chandra P, Ku[ik L, Robinson W H, Arend W P, Thompson P R, Holers V M. N-a-benzoyl-N5-(2-chloro-1-iminoethyl)-L-ornithine amide, a protein arginine deiminase inhibitor, reduces the severity of murine collagen-induced arthritis. J Immunol. 2011; 186(7): 4396-4404.
28. Jenuwein T, Allis C D. Translating the histone code. Science. 2001; 293:1074-1080.
29. Kouzarides, T. Chromatin modifications and their function. Cell 2007; 128: 693-705.
30. Dieker J, Muller S. Epigenetic histone code and autoimmunity. Clin Rev Allergy Immunol 2010; 39: 78-84.
31. Nightingale K P, B. M., Eberharter A, Mamais A, Becker P B, Boyes J. Acetylation increases access of remodelling complexes to their nucleosome targets to enhance initiation of V(D)J recombination. Nucleic Acids Res 2007; 35: 6311-6321.
32. Borders C L Jr, Broadwater J A, Bekeny P A, Salmon J E, Lee A S, Eldridge A M, Pett V B. A structural role for arginine in proteins: multiple hydrogen bonds to backbone carbonyl oxygens. Protein Sci. 1994; 3(4): 541-548.
33. Wegner N, Lundberg K, Kinloch A, Fisher B, Malinstrom V, Feldmann M, Venables P J. Autoimmunity to specific citrullinated proteins gives the first clues to the etiology of rheumatoid arthritis, Immunol Rev. 2010; 233(1): 34-54.

What is claimed herein is:

1. A method of treating sepsis or septic shock in a subject in need thereof, the method comprising administering a therapeutically effective amount of an antibody reagent that specifically binds citrullinated histone H3 (citrulline 2+8+17).

2. The method of claim 1, wherein the antibody reagent specifically binds a citrullinated histone and does not specifically bind the corresponding uncitrullinated histone.

3. The method of claim 1, wherein the citrullinated histone is a circulating citrullated histone.

4. The method of claim 1, wherein the administration is intravenous.

5. The method of claim 1, wherein the subject is a subject identified to have an elevated level of citrullinated histone.

6. The method of claim 1, wherein the method is a method of treating sepsis.

* * * * *